United States Patent
Wachman et al.

(10) Patent No.: US 9,412,005 B2
(45) Date of Patent: Aug. 9, 2016

(54) USE OF ERROR IMAGE FOR UNMIXING ARTIFACT REMOVAL IN LINEAR SPECTRAL UNMIXING

(71) Applicant: GOOCH & HOUSEGO PLC, Ilminster, Somerset (GB)

(72) Inventors: Elliot S. Wachman, Lakewood, NJ (US); Joel M. Recht, Monsey, NY (US)

(73) Assignee: Gooch & Housego PLC, Somerset (GB)

( * ) Notice: Subject to any disclaimer, the term of this patent is extended or adjusted under 35 U.S.C. 154(b) by 427 days.

(21) Appl. No.: 14/101,931

(22) Filed: Dec. 10, 2013

(65) Prior Publication Data

US 2015/0117744 A1 Apr. 30, 2015

Related U.S. Application Data (60) Provisional application No. 61/895,619, filed on Oct. 25, 2013.

(51) Int. Cl.
| | |
|---|---|
| *G06K 9/00* | (2006.01) |
| *G06K 9/46* | (2006.01) |
| *G01N 21/64* | (2006.01) |
| *G06K 9/38* | (2006.01) |

(52) U.S. Cl.
CPC ........ *G06K 9/00127* (2013.01); *G06K 9/00147* (2013.01); *G06K 9/4604* (2013.01); *G01N 21/6458* (2013.01); *G01N 2021/6441* (2013.01); *G06K 9/38* (2013.01)

(58) Field of Classification Search
None
See application file for complete search history.

(56) References Cited

U.S. PATENT DOCUMENTS

| | | | | |
|---|---|---|---|---|
| 6,008,492 | A | * | 12/1999 | Slater ........................ G01J 3/02 250/334 |
| 6,341,257 | B1 | | 1/2002 | Haaland |
| 6,415,233 | B1 | | 7/2002 | Haaland |
| 6,608,931 | B2 | * | 8/2003 | Sunshine ............... G01N 21/31 382/191 |
| 6,687,620 | B1 | | 2/2004 | Haaland et al. |
| 6,711,503 | B2 | | 3/2004 | Haaland |
| 6,741,740 | B2 | | 5/2004 | Sunshine et al. |
| 6,842,702 | B2 | | 1/2005 | Haaland et al. |
| 6,922,645 | B2 | | 7/2005 | Haaland et al. |
| 7,085,416 | B2 | | 8/2006 | Sunshine et al. |
| 7,316,904 | B1 | | 1/2008 | Farkas et al. |
| 7,321,691 | B1 | * | 1/2008 | Sunshine ............. G06K 9/0063 382/191 |
| 7,321,791 | B2 | | 1/2008 | Levenson et al. |
| 7,680,337 | B2 | | 3/2010 | Gruninger et al. |
| 8,110,159 | B2 | | 2/2012 | Wachman et al. |

(Continued)

OTHER PUBLICATIONS

United States Patent Office Action for U.S. Appl. No. 14/104,565 dated Aug. 13, 2015 (11 pages).

(Continued)

*Primary Examiner* — Vu Le
*Assistant Examiner* — Alexander J Lesnick
(74) *Attorney, Agent, or Firm* — Michael Best & Friedrich LLP (57) ABSTRACT

A method of removing a potential false positive result in a stained sample. The method includes the steps of: acquiring a spectral image set of a stained sample; performing linear spectral unmixing of the spectral image set to obtain a plurality of rule images; calculating an error image for the stained sample; thresholding at least one of the plurality of rule images, wherein thresholding is based on the error image; and removing a potential false positive result from the at least one of the plurality of rule images based on thresholding.

26 Claims, 4 Drawing Sheets

(56) References Cited

U.S. PATENT DOCUMENTS

| | | |
|---|---|---|
| 8,280,140 B2 | 10/2012 | Levenson et al. |
| 8,385,615 B2 | 2/2013 | Levenson et al. |
| 8,391,961 B2 | 3/2013 | Levenson et al. |
| 8,462,981 B2 | 6/2013 | Determan et al. |
| 9,064,308 B2 * | 6/2015 | Flanders ............... G06T 5/002 |
| 2006/0019409 A1 | 1/2006 | Nelson et al. |
| 2009/0214084 A1 * | 8/2009 | Asner ............... G06K 9/00657 382/110 |
| 2010/0014157 A1 | 1/2010 | Nolte et al. |
| 2010/0075373 A1 | 3/2010 | Hoyt |
| 2010/0246907 A1 | 9/2010 | Wachman et al. |
| 2012/0264110 A1 | 10/2012 | Wachman et al. |
| 2013/0230230 A1 * | 9/2013 | Ajemba ............... G06T 7/0012 382/133 |

OTHER PUBLICATIONS

Co-pending U.S. Appl. No. 14/104,565, filed Dec. 12, 2013.

* cited by examiner

USE OF ERROR IMAGE FOR UNMIXING ARTIFACT REMOVAL IN LINEAR SPECTRAL UNMIXING

CROSS-REFERENCE TO RELATED APPLICATIONS

This application claims priority to U.S. Provisional Patent Application No. 61/895,619 filed Oct. 25, 2013, the content of which is incorporated herein by reference in its entirety.

BACKGROUND

Embodiments of the invention relate to linear spectral unmixing and the reduction of artifacts in samples such as multiply-stained clinical samples where such artifacts can lead to false identification of disease.

A spectral image "cube" consists of a set of images each acquired at a different wavelength. Spectral image sets can be acquired of samples that are reflective, transmissive, or fluorescent. In many cases of interest, the final acquired image arises from the combined effect of various independent, often co-localized, spectrally-varying components present in the sample or scene being imaged. In linear spectral unmixing (LSU), it is assumed that the final acquired spectral image cube may be expressed as a linear combination of the contribution from each of these independent elements (the "reference spectra"). The mathematics of LSU allows the final image to be decomposed into separate "rule images", one for each reference spectrum, with the pixel-by-pixel intensity of each rule image corresponding to the relative amount of that spectral component calculated to be present in the acquired image.

SUMMARY

This Summary is provided to comply with 37 C.F.R. §1.73, presenting a summary of the invention to briefly indicate the nature and substance of the invention. It is submitted with the understanding that it will not be used to interpret or limit the scope or meaning of the claims In one embodiment, the invention provides a method of removing a potential false positive result in a stained sample. The method includes the steps of: acquiring a spectral image set of a stained sample; performing linear spectral unmixing of the spectral image set to obtain a plurality of rule images; calculating an error image for the stained sample; thresholding at least one of the plurality of rule images, wherein thresholding is based on the error image; and removing a potential false positive result from the at least one of the plurality of rule images based on thresholding.

In another embodiment the invention provides a method of a system for removing a potential false positive result in a stained sample. The system includes an image acquisition system and a controller operatively coupled to the image acquisition system, where the controller includes a microprocessor coupled to a memory. The controller is configured to acquire a spectral image set of a stained sample, perform linear spectral unmixing of the spectral image set to obtain a plurality of rule images, calculate an error image for the stained sample, threshold at least one of the plurality of rule images, wherein thresholding is based on the error image, and remove a potential false positive result from the at least one of the plurality of rule images based on thresholding.

Other aspects of the invention will become apparent by consideration of the detailed description and accompanying drawings.

BRIEF DESCRIPTION OF THE DRAWINGS

FIG. 3a illustrates the Hematoxylin rule image in a Pap-stained sample when only the four component Pap stain spectra are used for unmixing; FIG. 3b illustrates this same cell when two biomarker stain spectra are included in the unmixing.

FIG. 4a is the residual signal from the first additional biomarker, FIG. 4b is the residual signal from the second additional biomarker, and FIG. 4c (same as 3b) is the degraded Hematoxylin image resulting from unmixing with the four Pap spectra and the two additional biomarker spectra when no biomarkers are present. FIG. 4d is the arithmetic addition of 4a-4c and 4e (same as 3a) is the Hematoxylin rule image obtained when only the four Pap spectra are used for the unmixing.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events.

Furthermore, not all illustrated acts or events are required to implement a methodology in accordance with the present invention.

Embodiments of the invention relate to linear spectral unmixing (LSU) and the reduction of artifacts in samples such as multiply-stained clinical samples, particularly those where said multiple stains are transmission stains, and where such artifacts can lead to false identification of disease.

Using rule image values, one may obtain the LSU-calculated spectrum at each pixel by multiplying the rule image values at each pixel times the respective reference spectra. In addition, the LSU rms (root mean square) error image may be computed by calculating the square root of the sum of the squares of the difference between the LSU-calculated spectrum and the actual measured spectrum at each pixel location. Non-zero error at a particular pixel location may arise from one of several sources: a) measurement noise, b) the use of incorrect reference spectra; c) the failure to include a reference spectrum that is actually present; d) breakdown of the linearity assumption of the LSU mathematics due to various causes. Unlike the noise contribution to the rms error image, which generally appears as a "salt and pepper" pattern, the other three contributions listed above can lead to consistently high error values at specific areas in the image.

The error image has been used to identify regions where a reference spectrum was determined incorrectly or omitted entirely ('b' and 'c' above) in order to uncover regions requiring further investigation (see, for example, Slater et al, U.S. Pat. No. 6,008,492). The error image has also been used to determine reliability of previously identified spectral components (Determan, U.S. Pat. No. 8,462,981). Additionally, much work has been done using the error image to help determine optimum reference spectra when they are not known a priori (as in Levenson U.S. Pat. Nos. 8,385,615; 8,280,140; Gruninger U.S. Pat. No. 7,680,337; Sunshine U.S. Pat. Nos. 7,321,691; 7,085,416; 6,741,740; 6,608,931), or ('d' above) to develop augmented iterative non-standard LSU algorithms to model such samples (as in Haaland U.S. Pat. Nos. 6,922,645; 6,842,702; 6,711,503; 6,687,620; 6,415,233; 6,341,257).

The inventors have recognized an additional use of the error function in instances in which all reference components are known, where their respective reference spectra are also known, and where the stains themselves and in combination with each other are known to behave linearly. The most common example of this situation occurs in spectral imaging of clinical and biological samples, in which a sample is typically labeled with various known stains specific to the molecular, chemical or structural moieties of interest. The reference spectra present in the sample are all known (since they have been placed there at the time of sample preparation) and can be all well characterized (by measuring their spectra individually). Further, in transmission stained samples, these stains can be chosen to have minimal spectral change with stain concentration and to have minimal interaction with each other. In fluorescence stained samples, interactions between stains can also be minimized, although one also has to take into account sample autofluorescence.

The inventors have observed that, notwithstanding the discussion above, high error locations do exist in these samples as well, and they can be used to minimize unmixing artifacts that can compromise the utility of LSU in applications such as spectral unmixing of clinical samples, in which accurate interpretation is of the utmost importance.

Accordingly, disclosed herein are methods and systems for identifying false-positive results using the LSU error image. Embodiments of the present invention describe methods of using the LSU error image for removing unmixing artifacts in multiply-stained samples where the reference spectra are all known and are all well-defined. LSU may be used to generate the calculated spectrum at each pixel in the image and the rms error between this calculated spectrum and the actual measured spectrum can then be computed for each pixel, thereby producing the rms error image. Choice of a suitable error value can be used as a threshold, $T_0$, for this error image wherein error values below $T_0$ become part of the binary Low Error image and those above $T_0$ become part of the binary High Error image. A rule image calculated by the LSU algorithm can then be subjected to a second dual threshold filtering process wherein those pixels corresponding to '1' in the Low Error image are required to have rule image values above a certain threshold value, $T_1$, and those corresponding to '1' in the High Error image are required to have rule image values above a second threshold value, $T_2$, where $T_2 > T_1$.

In one embodiment, the invention provides a method for removing unmixing artifacts from multiply stained clinical biological samples. One such example is a cervical cell sample stained with Papanicolaou (Pap) stain and with additional transmission stains attached to one or more biomarkers relevant to the presence, staging or progression of cervical cancer. In such samples, the rule images corresponding to said biomarkers are important determiners of potential abnormality and it is critical that non-zeros values of these biomarkers in cellular locations in these rule images not have contributions due to unmixing artifacts. Dual thresholding based on the LSU rms error image can be used to effectively remove such artifacts.

In multiply-stained transmission samples the inventors have found that high error locations most often coincide with structural anomalies in the cell, such as regions having unusual cytoplasmic folding, cell clumping, or atypical nuclear or cytoplasmic membrane edges; additionally, these effects often, but not always, lead to a greater than average uptake of stain. Without being limited as to the theory, a possible explanation for this correlation is that these anomalies lead to a high degree of scattering which results in a wavelength-dependent variation of the acquired signal not accounted for in the standard LSU methodology—thereby leading to a higher than average LSU error value at that location.

Whereas the error image has been used in some situations to extend the LSU algorithm beyond its conventional closed-form mathematical paradigm, as mentioned above, this complication is unnecessary and overly time-consuming for many applications, including multiply-stained clinical samples.

When performing LSU on a sample using a known reference spectra set, the LSU algorithm may sometimes produce a non-zero value for each of the reference spectra being used, even when that particular spectrum is not present at the pixel in question. Typically, such non-zero "unmixing crossover" values are quite small in magnitude and simple thresholding is adequate to eliminate this potential source of false positive results.

However, in structurally anomalous regions such as those mentioned above in which error values are particularly high, the values associated with such unmixing crossover can be considerably elevated. Heuristically, this may be understood to result from the LSU algorithm attempting to use all reference spectra at its disposal to match as best as possible the extra scattering term at these high error pixel locations.

If a single threshold value is used to distinguish between true and false biomarker staining throughout the entire sample, it is likely that false positive biomarker results will result at all high error value locations on the slide, resulting in many "false positive" locations, a situation untenable for clinical applications. Accordingly, by segmenting the image into "low error" and "high error" locations using an empirically derived error value threshold, the inventors have found that they can assign separate biomarker stain thresholds for low and high error locations, and in so doing, significantly reduce the number of false positive regions identified without unduly compromising identification of the true positive biomarker locations.

Figure 1:
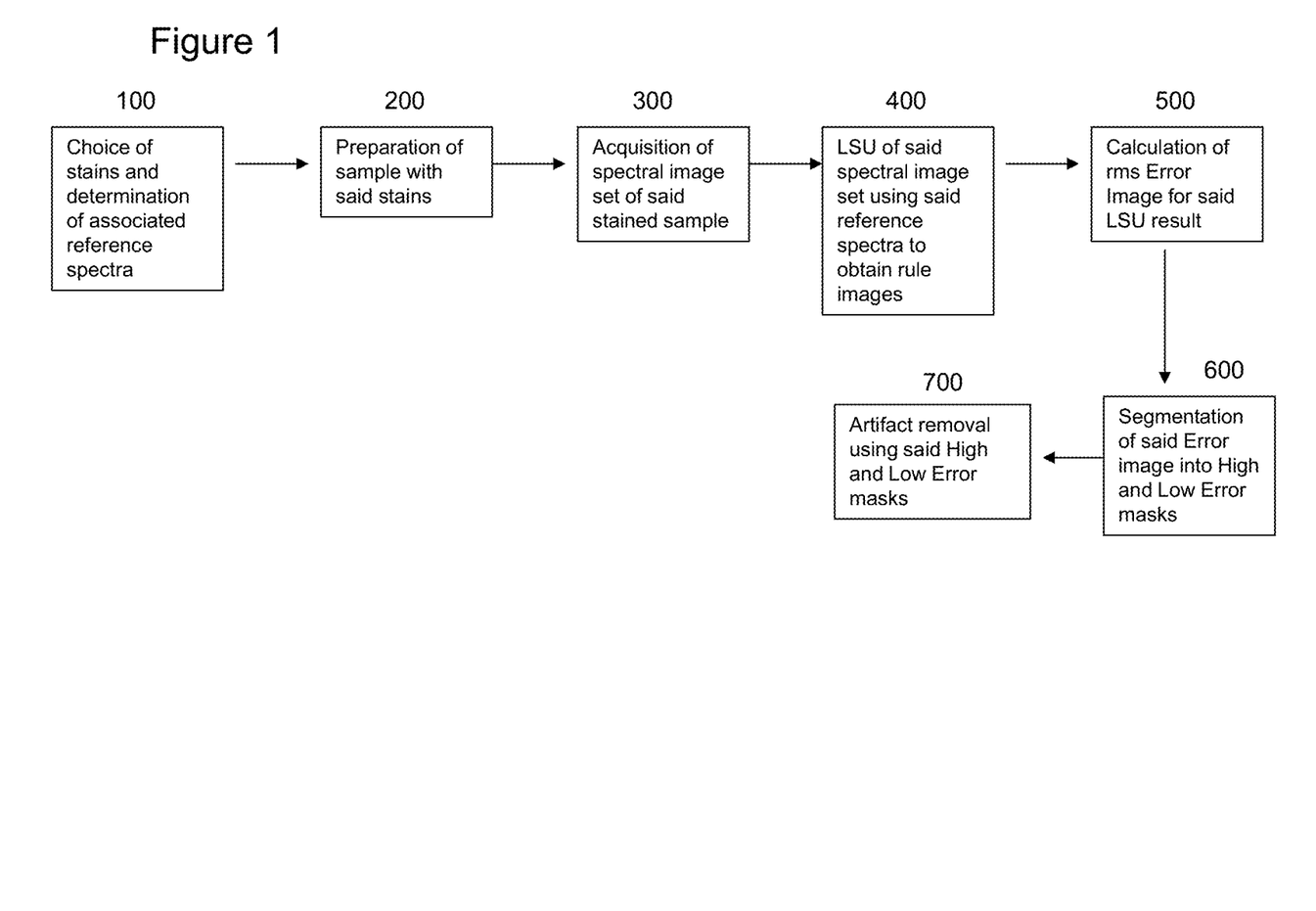
FIG. 1 is a flow chart describing the various steps according to embodiments of the invention.

The general methodology of this invention is shown in FIG. 1. In step 100, the specific multiple stains to be used for preparation of the sample are chosen. To the extent possible, these stains are chosen to minimize spectral overlap between them, although in practice choices are often limited. It is further important to choose stains known to have minimal spectral variation with concentration and to have minimal non-linear reactivity with each other. Although the examples disclosed herein focus on samples that are labeled with transmission stains, the disclosed procedures can also be used on samples that are labeled with fluorescent dyes. Samples may be prepared according to methods disclosed in US Patent Appl. Publ. No. 20120264110, which is incorporated herein by reference in its entirety.

A sample can include any imaged object, whether biological or not. Biological samples can include a solution with single cells or groups of cells as well as tissues. The sample may be single cells and/or groups of cells that are spread onto a substrate, such as a coverslip or microscope slide, or may also include tissues, including sectioned tissues, that are mounted onto a substrate such as a coverslip or microscope slide.

Stains may include general stains such as hematoxylin (blued or unblued), eosin, or combinations of such stains (such as Papanicolaou stain), which label all or most cells. Other general stains include Alcian blue, PAS (with and without diastase pretreatment), trichrome, reticulin, Prussian blue, gram stain, and Grocott methenamine silver. Stains may also include a specific label such as an antibody or nucleotide probe which is directed to a particular structure(s) or chemical(s), generally with a high degree of specificity. The specific labels in turn may be directly or indirectly coupled to a marker such as a fluorescent dye, or an enzyme or other means for generating a dye such as a localized precipitate (e.g. DAB). A specific label may have a marker (a dye or an enzyme or other means for generating a dye) directly coupled to the specific label or indirectly, for example a secondary antibody which binds to a specific label such as a primary antibody, where the secondary antibody has a marker attached thereto. Fluorescent probes that may be used include organic dyes such as DAPI, FITC, Rhodamine, Cyanine dyes, etc.; quantum dots; and phosphorescence probes. Transmission stains that may be used include DAB, AEC, Space Black, Ferangi Blue, True Blue, Fast Red, Warp Red, etc.

In step 200, the sample is prepared with these stains. For multiply-stained transmission samples, if the staining intensity is too dark the acquired signal level will be greatly reduced, thereby increasing noise of the unmixing. It is therefore desirable in such samples to reduce staining intensities to the extent possible.

In step 300, a spectral image set of the sample prepared in step 200 is acquired. The sample may be illuminated with UV, visible, and/or infrared light as appropriate and images of the sample may be collected at varying wavelengths or bands of wavelengths. Illuminating and/or collecting images of the sample at varying wavelengths may be performed using bandpass filters, e.g. on a slider or filter wheel; using an acousto-optical tunable filter (AOTF) device; a liquid crystal tunable filter (LCTF); Sagnac-interferometer Fourier systems; tomographic imagers; "push-broom" imaging devices of all types; a collection of interference filters (including those placed as a thin-film mask placed over an imaging device (e.g. a CCD chip) such as in a Bayer pattern or in other types of masking. In various embodiments a spectral image may include a set of images obtained at wavelengths across the visible spectrum, e.g. from 460 to 730 nm at 10 nm intervals, although other wavelength ranges and intervals are also possible.

Methods for preparing samples, collecting images, and processing image data can be found in US Patent Appl. Publ. No. 2010/0246907, and U.S. Pat. No. 7,316,904, each of which is incorporated herein by reference in its entirety.

In step 400, linear spectral unmixing of the image set acquired in step 300 is performed using methods known to those skilled in the art. Rule images are obtained for each reference spectrum, wherein the value at any pixel of a given rule image indicates the relative amount of that reference component at said pixel. Using the reference spectra, this information can be used to compute the LSU-calculated spectrum at each pixel in the image. In various embodiments, each rule image pixel value is a number between 0 and 1 which indicates the fraction of the raw data that corresponds to a given reference spectrum at that pixel. In theory, it should be possible to faithfully reconstruct the originally-collected spectral data by combining the rule images with the information in the reference spectra (referred to herein as the LSU-calculated spectrum). Non-zero values in the Error Images show the extent to which this reconstruction of the data differs from the original data. Some of the Error Image non-zero values correspond to general system noise; these values tend to fluctuate between adjacent pixels and give rise to "salt and pepper" noise patterns. Other Error Image non-zero values are associated with a particular portion of the sample and can falsely give rise to positive indications that a disease marker is present at that portion of the sample. Thus the objective is to identify such regions of the Error Image in an objective and systematic manner and to use this information to reduce or eliminate false positive results.

In step 500, the rms Error Image is calculated from the results of step 400. The Error Image is found by calculating the square root of the sum of the squares of the difference between the LSU-calculated spectrum of step 400 and the actual measured spectrum at each pixel location found in 300. In some embodiments, a smoothing step such as a 3×3 or 5×5 median filter, a Gaussian convolution filter, or a similar type of noise reducing filter may be applied to the Error Image to remove effects of noise.

In step 600, an empirically derived threshold, $T_0$, is used to segment the Error Image into two binary images, a High Error image mask and a Low Error image mask, with the High Error image mask corresponding to regions in the Error Image above said empirically derived threshold $T_0$, and the Low Error image mask corresponding to regions in the Error Image below said empirically derived threshold $T_0$. In various embodiments, values equal to the threshold $T_0$ may be assigned to one or the other of the Low Error mask or the High Error mask. The actual threshold value $T_0$ to be used in a particular case may be found by examining the error images from a number of (e.g. 5-10) test locations across the slide and determining the lowest threshold value which eliminates most or all of the random-noise related error. Random noise error typically appears as separated pixels of non-zero values in the error image in a "salt and pepper" pattern. When $T_0$ is found, these isolated pixels will be removed, i.e. zeroed out, and only localized clusters of high error values will remain. The lowest value which removes the vast majority (e.g. at least 95%) of the random noise error in the images from these test locations is the proper choice for $T_0$.

In step 700, said High Error and Low Error image masks are used to remove artifactual results from specific rule images generated in step 400 as follows: a) the High Error and Low Error image masks are separately applied to different copies of the rule image of interest to create high and low error rule images, respectively; b) pixels in the low error rule image are required to have rule image values above a certain threshold value, $T_1$, and pixels in the high error rule image are required to have rule image values above a second threshold value, $T_2$, where $T_2 > T_1$, where $T_1$ is chosen to remove at least 90% of unmixing artifact signal observed in Low Error regions, and $T_2$ is chosen to remove at least 90% of unmixing artifact signal observed in High Error regions, as will be described below; c) the results of this dual thresholding of the rule image generate the final rule image in which unmixing artifacts have been largely removed. Application of the $T_1$ threshold to the low error rule image produces a low error thresholded image; application of the $T_2$ threshold to the high error rule image produces a high error thresholded image. The low error thresholded image and the high error thresholded image are then added together to produce the final rule image, also referred to as a masked rule image.

Figure 2:
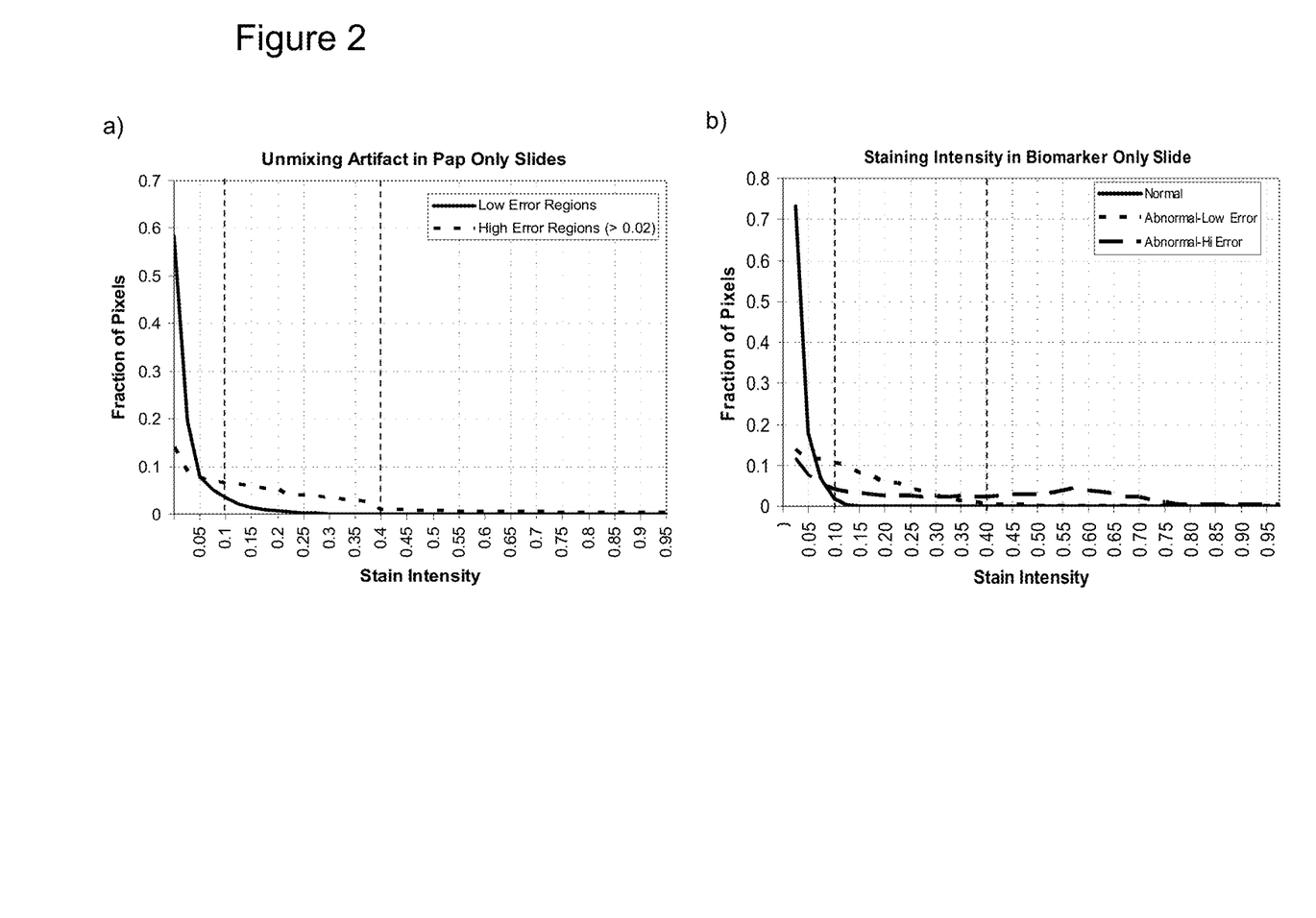
FIG. 2a is a graph illustrating the distribution of biomarker stain values due purely to artifact in the unmixing process, as measured on a slide not containing any biomarker staining, and the difference in this distribution between low error and high error regions of the slide.
FIG. 2b illustrates the range of actual biomarker staining intensity on a slide with a variety of biomarker-positive cells, and the difference in this distribution in normal cells (so-called background staining), and abnormal cells in both low and high error regions.

The use of a higher threshold, $T_2$, in High error regions is effective in removing unmixing artifacts as shown in FIG. 2a. In this figure, cervical cell slides stained with Pap stain only were unmixed using four reference spectra for each of the Pap stain components (Hematoxylin, Eosin Y, OG6, and Fast Green) plus a fifth reference spectra for an additional biomarker (which in this case was not present). Whereas in principle the biomarker stain values should be zero at all pixels in the image, the LSU unmixing artifact mentioned above produces non-zero values in many cellular locations, with these values much higher in High Error regions as shown in the figure. In particular, the figure displays normalized histograms for the biomarker stain values for both Low Error and High Error regions. Note that whereas in this example a Low Error threshold of 0.1 would effectively remove most of the unmixing artifact in such regions (left dotted vertical line), it would not be sufficient to remove the artifact in the High Error regions. The High Error regions would require a threshold of 0.4 in order to effectively remove artifact (right dotted vertical line).

In some embodiments, instead of using a series of separate threshold values and masking steps, a threshold value can be constructed which is a function of the error image, T(E), and which is applied to the rule images to achieve a result that is equivalent to what is obtained using the separate steps outlined above. More generally, an Error Threshold Image can be created, wherein the value at a given pixel in this image is an arbitrary function of the value of the Error Image at the location of said pixel. This Error Threshold Image can now be applied to the rule image of interest, so that only pixels whose rule image values are greater than the error threshold image value at that pixel location are included in the final masked rule image. Thus, $T_1$ and $T_2$ are not simply made to be variable, but $T_0$, $T_1$, and $T_2$ are replaced with a function $T(E)$, where E is the error value at a given pixel and T is the corresponding threshold value for that pixel. Hence, for the case illustrated above: $T(E)=T_1$ for $E<T_0$ and $T(E)=T_2$ for $E>T_0$.

This dual threshold approach based on the Error image will only be effective, of course, if the threshold values used are not so high that they will prevent the detection of true positive biomarker staining. There are, however, various means of increasing specific positive staining intensities while keeping background non-specific staining at a low level, as is known to those skilled in the art. A representative illustration of this approach is shown in FIG. 2b. To produce this figure, an abnormal cervical cell sample was immunohistochemically labeled for the biomarker p16 using Space Black stain (Biocare Medical, Concord, Calif.). The values of the biomarker stain intensity in positive and negative cells was measured and the intensity histogram compiled, as shown in the Figure. These results indicate that background non-specific staining in negative cells is largely eliminated using a threshold of 0.1, whereas the value of the specific positive biomarker staining is largely above 0.1 in low error regions and largely above 0.4 in high error regions. In this example, therefore the choice of $T_1$=0.1 and $T_2$=0.4 should result in effective artifact removal without unduly compromising detection of true positive staining.

Figure 3:
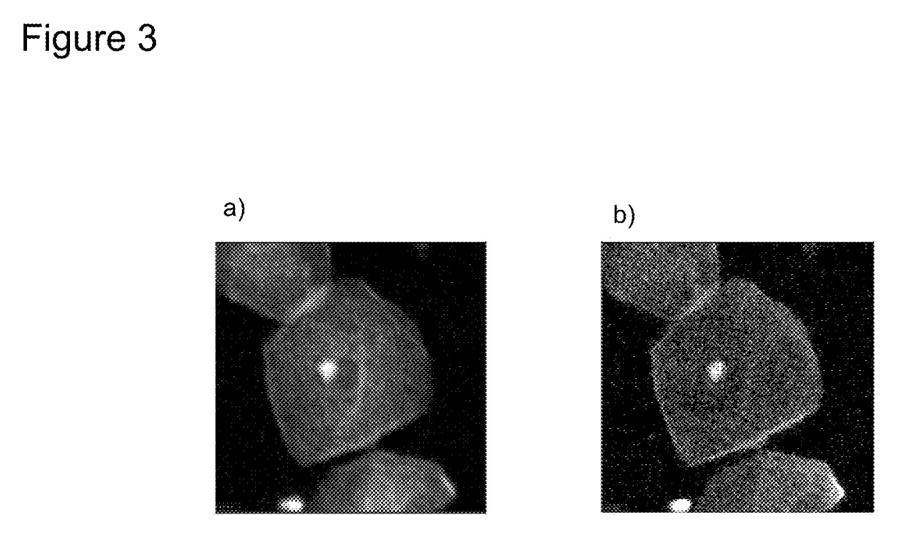
FIG. 3 illustrates that unmixing artifact can also occur in regions where biomarker is not present, such that the detection of the non-biomarker stains of a multiply-stained sample is degraded when unmixing is performed with spectra that are not actually present at that location.
Figure 4:
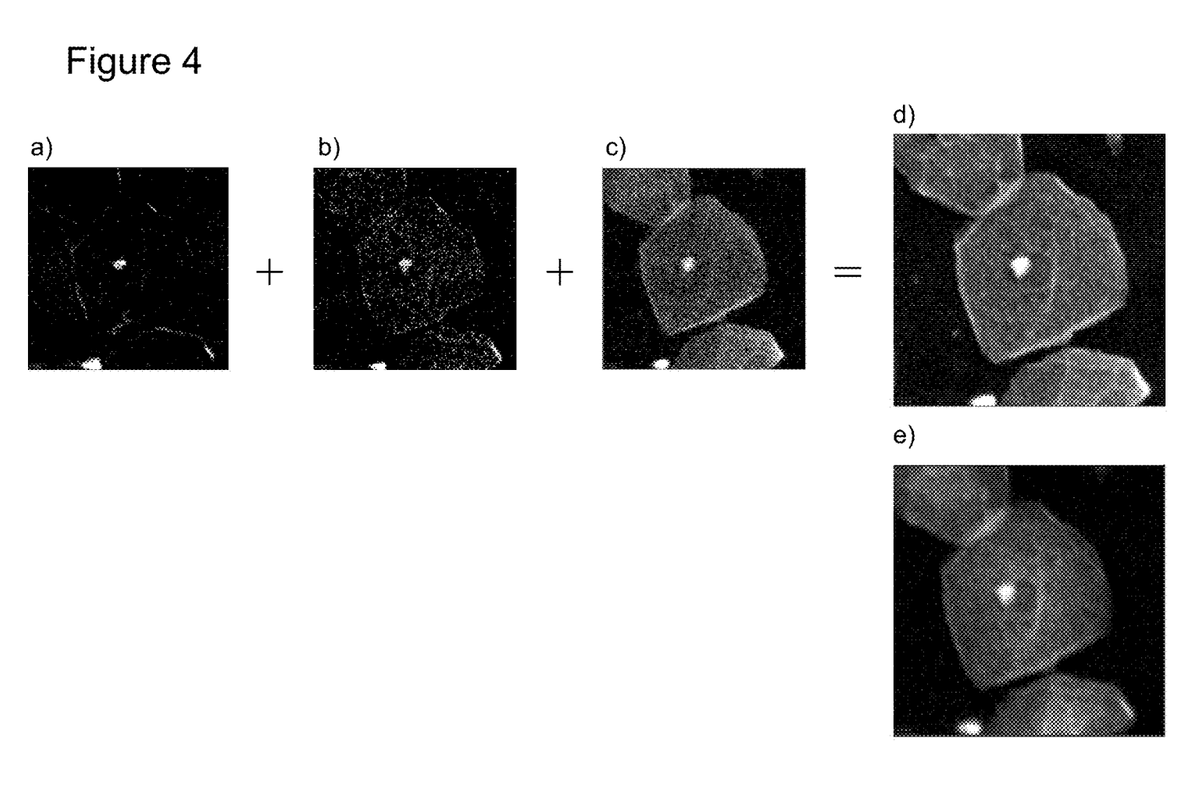
FIG. 4 illustrates that the degradation of FIG. 3 can be corrected in its entirety by arithmetic addition of the residual signals, present in the additional biomarker stain rule images, to the original degraded image.

As mentioned, regions in which no true positive biomarker staining is present will nonetheless often have non-zero values of biomarker identified by the LSU algorithm. These values can be removed by the thresholding procedure described above, however when this occurs there is a corollary degradation of the rule images of the reference components that are actually present. The inventors have found that once identified as false, these biomarker values can be added back into the rule images of the reference components known to be present at that location. Through this process the degradation in these reference components that are present can be completely corrected. An example of this is shown in FIG. 3, where a cervical cell stained with Pap stain is unmixed a) with the four reference spectra corresponding to the primary components of the Pap stain that are actually present; and in b) with two additional reference spectra corresponding to biomarkers that are not present in the cell. In FIG. 3a, the primary Hematoxylin rule image of the Pap stain combination is shown. The degradation due to the inclusion of the two additional spectra is evident in the degradation of the cytoplasmic detail in 3b. In FIG. 4, the artifactual rule images for the additional reference spectra (4a, 4b) are then added back to the rule image of 3b (4c), resulting in the recovered Hematoxylin rule image (4d), which can be seen to compare favorably with the correct Hematoxylin rule image of 3a (4e).

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Various features and advantages of the invention are set forth in the following claims.

What is claimed is:

1. A method of removing a potential false positive result in a stained sample, the method comprising the steps of:
   acquiring a spectral image set of a stained sample;
   performing linear spectral unmixing of the spectral image set to obtain a plurality of rule images;
   calculating an error image for the stained sample;
   thresholding at least one of the plurality of rule images, wherein thresholding is based on the error image and further comprises segmenting the error image to create a high error mask image and a low error mask image; and separately applying both mask images to at least one of each of the plurality of rule images; and
   removing a potential false positive result from the at least one of the plurality of rule images based on thresholding.

2. The method of claim 1, wherein the stained sample comprises a sample labeled with a plurality of transmission stains.

3. The method of claim 2, wherein the plurality of transmission stains have a plurality of reference spectra associated therewith such that each transmission stain has a respective reference spectrum.

4. The method of claim 3, wherein each of the plurality of rule images comprises an array of proportional values representing proportions of the spectral image set that correspond to each of the reference spectra.

5. The method of claim 4, wherein calculating an error image for the stained sample comprises
   combining the information of each of the plurality of rule images with the respective reference spectrum to produce a calculated spectral image set, and
   determining a difference between the calculated spectral image set and the acquired spectral image set.

6. The method of claim 5, wherein combining the information of each of the plurality of rule images with the respective reference spectrum comprises multiplying, on a pixel by pixel basis, each of the plurality of rule images times the respective reference spectrum and adding the results to produce the calculated spectral image set.

7. The method of claim 6, wherein calculating an error image for the stained sample further comprises calculating, on a pixel by pixel basis, a root-mean-square value of the difference.

8. The method of claim 7, wherein segmenting the error image to create at least one mask image comprises
   identifying a first threshold value, and
   applying the first threshold value to the error image such that pixels within the error image below the first threshold value are used to create a binary low error image mask and pixels above the first threshold value are used to create a binary high error image mask.

9. The method of claim 8, further comprising
   applying the binary low error image mask to at least one of the plurality of rule images to create a low error rule image, and
   applying the binary high error image mask to at least one of the plurality of rule images to create a high error rule image.

10. The method of claim 9, further comprising
    applying a second threshold value to the low error rule image to create a low error thresholded image, and
    applying a third threshold value to the high error image to create a high error thresholded image.

11. The method of claim 10, further comprising combining the low error thresholded image and the high error thresholded image to create a masked rule image.

12. The method of claim 1, wherein thresholding at least one of the plurality of rule images comprises applying a threshold function $T(E)$ to the at least one of the plurality of rule images, wherein the threshold function $T(E)$ is based on the error image.

13. The method of claim 1, wherein the stained sample comprises cervical cells.

14. A system for removing a potential false positive result in a stained sample, comprising:
    an image acquisition system; and
    a controller operatively coupled to the image acquisition system, the controller having a microprocessor coupled to a memory, the controller configured to
    acquire a spectral image set of a stained sample, perform linear spectral unmixing of the spectral image set to obtain a plurality of rule images,
    calculate an error image for the stained sample,
    threshold at least one of the plurality of rule images, wherein thresholding is based on the error image and further comprises segmenting the error image to create a high error mask image and a low error mask image; and separately applying both mask images to at least one of each of the plurality of rule images; and
    remove a potential false positive result from the at least one of the plurality of rule images based on thresholding.

15. The system of claim 14, wherein the stained sample comprises a sample labeled with a plurality of transmission stains.

16. The system of claim 15, wherein the plurality of transmission stains have a plurality of reference spectra associated therewith such that each transmission stain has a respective reference spectrum.

17. The system of claim 16, wherein each of the plurality of rule images comprises an array of proportional values representing proportions of the spectral image set that correspond to each of the reference spectra.

18. The system of claim 17, wherein, to calculate an error image for the stained sample, the controller is further configured to
    combine the information of each of the plurality of rule images with the respective reference spectrum to produce a calculated spectral image set, and
    determine a difference between the calculated spectral image set and the acquired spectral image set.

19. The system of claim 18, wherein, to combine the information of each of the plurality of rule images with the respective reference spectrum, the controller is further configured to multiply, on a pixel by pixel basis, each of the plurality of rule images times the respective reference spectrum and add the results to produce the calculated spectral image set.

20. The system of claim 19, wherein, to calculate an error image for the stained sample, the controller is further configured to calculate, on a pixel by pixel basis, a root-mean-square value of the difference.

21. The system of claim 20, wherein, to segment the error image to create at least one mask image, the controller is further configured to
identify a first threshold value, and
apply the first threshold value to the error image such that pixels within the error image below the first threshold value are used to create a binary low error image mask and pixels above the first threshold value are used to create a binary high error image mask.

22. The system of claim 21, wherein the controller is further configured to
apply the binary low error image mask to at least one of the plurality of rule images to create a low error rule image, and
apply the binary high error image mask to at least one of the plurality of rule images to create a high error rule image.

23. The system of claim 22, wherein the controller is further configured to
apply a second threshold value to the low error rule image to create a low error thresholded image, and
apply a third threshold value to the high error image to create a high error thresholded image.

24. The system of claim 23, wherein the controller is further configured to combine the low error thresholded image and the high error thresholded image to create a masked rule image.

25. The system of claim 14, wherein, to threshold at least one of the plurality of rule images, the controller is further configured to apply a threshold function T(E) to the at least one of the plurality of rule images, wherein the threshold function T(E) is based on the error image.

26. The system of claim 14, wherein the sample comprises cervical cells.

* * * * *